United States Patent [19]

Hibberd et al.

[11] Patent Number: 4,581,847
[45] Date of Patent: Apr. 15, 1986

[54] TRYPTOPHAN OVERPRODUCER MUTANTS OF CEREAL CROPS

[75] Inventors: Kenneth A. Hibberd, Falcon Heights; Paul C. Anderson, Minneapolis; Melanie Barker, Bloomington, all of Minn.

[73] Assignee: Molecular Genetics Research and Development, Minnetonka, Minn.

[21] Appl. No.: 647,008

[22] Filed: Sep. 4, 1984

[51] Int. Cl.$^4$ ............................................. A01H 1/06
[52] U.S. Cl. ..................................................... 47/58
[58] Field of Search ............................................. 47/58

[56] References Cited

U.S. PATENT DOCUMENTS 4,443,971 4/1984 Chaleff.

OTHER PUBLICATIONS

Processed Plant Protein Foodstuffs, Altschul, 1958, Acad. Press, Inc., New York, pp. 878–880, 883, 884, and 891 cited.
Amino Acids, Nutrition and Stress, Miflin et al., pp. 391–414, Genetic Eng. of Plants, 1983, Plenum Press, N.Y.
Selection of Plant Cell Lines, Widholm, pp. 99–113, Plant Tissue Culture as a Source of Biochemicals, 1980, CRC Press.
Handbook of Plant Cell Culture, Evans et al., 1983, Macmillan Publ. Co., N.Y., pp. 43–45, 50, 401.
Widholm, Biochim. Biophys. Acta, 261: 44–51, 52–58, (1972).
Widholm, Biochim. Biophys. Acta, 279: 48–57 (1972).
Singh and Widholm, Biochem. Gen. 13: 357–367 (1975).
Carlson and Widholm, Physiol. Plant 44: 251–255 (1978).
Ranch et al., Plant Physiol. 71: 136–140 (1983).
Chaleff and Ray, Science, 233: 1148–1153, (1984).

*Primary Examiner*—Robert Bagwill
*Attorney, Agent, or Firm*—Pennie & Edmonds

[57] ABSTRACT

This invention is directed to the production of novel plant genotypes or lines which produce increased free tryptophan levels and are resistant to inhibition by analogs which normally inhibit the activity of the enzyme anthranilate synthase before alteration. This invention further relates to genes encoding such enzymes, and to processes for utilizing these novel genes and enzymes. Further products of the invention include plants, plant tissues and seeds which exhibit resistance to such analogs and overproduce tryptophan resulting from expression of genes encoding analog resistant anthranilate synthase enzyme.

32 Claims, 5 Drawing Figures

TRYPTOPHAN OVERPRODUCER MUTANTS OF CEREAL CROPS

TABLE OF CONTENTS

FIELD OF THE INVENTION
BACKGROUND OF THE INVENTION
   Tissue Culture of Maize
   Tryptophan Biosynthesis
   Resistance to Inhibition by Tryptophan Analogs
SUMMARY OF THE INVENTION
BRIEF DESCRIPTION OF THE FIGURES
DETAILED DESCRIPTION OF ONE EMBODIMENT OF THE INVENTION
   Strategy for Selection of Tryptophan Overproducer Cell Lines
   Selection and Characterization of Resistant Cell Lines
   Plant Regeneration and Production of Seed
   Development of Tryptophan Overproducer Commercial Hybrid Seed
   Alternate Methods of Obtaining Tryptophan Overproducer Mutants
   Commercial Approaches to Tryptophan Extraction from High Tryptophan Maize Seed
EXAMPLES
   Characterization of the Effects of 5-Methyltryptophan and Strategy for Selection of 5-Methyltryptophan Resistant Maize Cells
      Initiation and Maintenance of Maize Cell Cultures Which Retain Plant Regeneration Capacity
      Callus Culture Growth Inhibition by 5-Methyltryptophan
   Selection and Characterization of a 5-Methyltryptophan Resistant Cell Line
      Selection of 5-Methyltryptophan Resistant Cell Line
      Characterization of Maize Cell Line C28
      Analysis of Free Trytophan
      Anthranilate Synthase Assays
   Plant Regeneration and Production of Seed
      Plant Regeneration Protocol
      Characterization Of Progeny Plants and Seeds
      Analysis of Free Tryptophan
DEPOSIT OF SEEDS

FIELD OF THE INVENTION

This invention relates to novel plant genotypes or lines, and in particular novel monocots and other cereal crops, which produce increased levels of free tryptophan in callus cultures, plants, plant tissues and seeds. Also described are the processes for development and characterization of these novel genotypes. This trait is genetically transmitted to progeny. These lines may be used for human or animal consumption, or alternatively, as a source from which tryptophan may be extracted.

BACKGROUND OF THE INVENTION

Tissue Culture of Maize

Irrespective of the plant species, there are a number of common features that apply to most tissue culture programs. The technique of cell and tissue culture has been widely developed, and much work has been done on growth, metabolism and differentiation of tissue culture of dicotyledons (Yamada, 1977, in Plant Cell, Tissue and Organ Culture, Reinert and Bajaj (eds.), pp. 144-159, Springer-Verlag, Berlin). However, successful tissue culture studies with monocotyledons (e.g., the cereal crops such as maize, rye, barley, wheat, sorghum, oats, millet and rice) leading to plant regeneration are not as well documented. Success is frequently dependent on choosing donor tissues for culture initiation which come from plants of appropriate genotype as well as physiological and development states. Other features which are also important include the organic and inorganic composition of the growth medium and the physical environment in which the cultures are grown.

In maize, the development of tissue cultures capable of plant regeneration was accomplished after the identification of appropriate genotypes and donor tissues (Green and Rhodes, 1982 in Maize for Biological Research, W. F. Sheridan (ed.), pp. 367-371, Plant Molecular Biology Association, Charlottesville, Va.). The first method developed which yielded regenerated plants from tissue cultures of maize used immature embryos as donor tissues. With N6 or MS growth media (defined below in Section 6) and a synthetic auxin, such as 2,4-dichlorophenoxyacetic acid (2,4-D), tissue cultures develop rapidly from the scutellum of the embryos. The resulting cultures are developmentally heterogeneous and contain a variety of tissue types. Removal of the 2,4-D from the growth medium permits these cultures to produce large numbers of regenerated plants. Cultures of this type have proved capable of regenerating plants for up to three years.

Another donor tissue from which regenerable tissue cultures of maize have been initiated are immature tassels. This tissue is the male flower and as it matures it is responsible for pollen production. Immature embryos, influorescences, and the few other tissues in cereals from which regenerating cultures have been initiated all have the common characteristic of juvenility. Regenerated plants obtained from tissue cultures are grown to maturity in a glasshouse, growth chamber, or field. The progeny seed produced in crosses with regenerated plants permits the evaluation of subsequent generations. The basic tissue culture methods developed for corn have been extended to many other cereal species.

It is now possible to reliably initiate cultures of corn which have two important characteristics. One is that the callus cultures are friable, meaning that they are soft and loose in texture. This property is important because cultures of this type exhibit rapid growth and it facilitates the initiation of suspension cell cultures. The other valuable attribute of these friable cultures is their ability to form very large numbers of somatic embryos. Microscopic examination reveals the presence of many small, organized structures on the surface of the callus. These structures are young somatic embryos at various developmental stages. These friable cultures will retain their embryogenic potential for as long as two years and have shown the capacity to produce extremely large numbers of somatic embryos.

The somatic embryos in these friable calli develop to maturity when the cultures are transferred to medium containing 5 to 6 percent sucrose and no hormones. After approximately two weeks of growth on this medium, many embryos become quite mature. They germinate rapidly and grow into plants when placed on MS or N6 medium containing 2% sucrose. The plants can then be established in soil and grown to maturity.

It is now well-documented that a high level of genetic variability can be recovered from plant tissue culture.

Some of this variability is of agronomic importance. Mutants for disease resistance have been obtained in sugarcane for Fiji disease, early and late blight in potato, and southern corn leaf blight in maize. In rice, maize, and wheat considerable variability for traits inherited as single genes of plant breeding interest have been recovered, including those which control the time of seed set and maturation, seed color and development, plant height, plant morphology, and fertility.

Tissue cultures of maize have been used to recover mutants for disease resistance and amino acid overproduction as described below.

Texas male sterile cytoplasm (cms-T) genotypes of maize are susceptible to the pathotoxin produced by the fungus *Helminthosporium maydis* race T, while normal cytoplasm (N) genotypes are resistant (Gengenbach et al., 977, Proc. Natl. Acad. Sci. U.S.A. 74: 5113-5117). Similarly, tissue cultures obtained from cms-T genotypes are susceptible to the pathotoxin while N genotype cultures are resistant. The pathotoxin from *H. maydis* race T was used to select resistant cell lines from susceptible cms-T cultures using a sublethal enrichment selection procedure. After five cycles of increasing selection pressure, cell lines were recovered which were resistant to lethal levels of the pathotoxin. Plants regenerated from these cell lines also were resistant to the pathotoxin and were male-fertile. Genetic analysis of progeny obtained from resistant, male-fertile plants showed that both traits were maternally inherited. Infection of plants with *H. maydis* race T spores demonstrated that selection for pathotoxin resistance also resulted in resistance to the disease organism by plants.

Selection for resistance to growth inhibition by lysine plus threonine in equimolar concentrations (LT) in tissue cultures of maize yielded a stable resistant line, LT19 (Hibberd and Green, 1982, Proc. Natl. Acad. Sci. U.S.A. 79: 559-563). Genetic analysis of progeny of plants regenerated from LT19 showed that LT resistance was inherited as a single dominant nuclear gene. Tissue cultures initiated from resistant embryos required 5-10 times higher levels of LT to inhibit growth than did cultures from LT-sensitive embryos. LT resistance in LT19 was expressed as reduced sensitivity of root and shoot growth to the presence of LT. The free pool of threonine was increased 6 times in cultures initiated from immature embryos of LT-resistant plants, and 75-100 times in kernels homozygous for LT19, as compared to cultures and kernels from LT-sensitive embryos and plants, respectively. Overproduction of free threonine increased the total threonine content in homozygous LT19 kernels by 33-59%. The results demonstrate that LT resistance selected with tissue culture methods was heritable and was expressed in cultures, seedlings, and kernels.

Tryptophan Biosynthesis

The tryptophan biosynthetic pathway is initiated by the conversion of chorismate to anthranilate in a glutamine-dependent reaction. The phosphoribosyl moiety of phosphoribosyl pyrophosphate is then transferred to anthranilate. The indole ring is formed in two steps involving first an isomerization converting the ribose group to a ribulose and then a cyclization reaction to yield indole glycerol phosphate. The final reaction in the pathway is catalyzed by a single enzyme that may contain either one or two kinds of subunit. The reaction consists of the cleavage of indole glyceraldehyde-3-phosphate and condensation of the indole group with serine (Umbarger, 1978, in Ann. Rev. Biochem. 47: 555-606).

Metabolite flow in the tryptophan pathway in higher plants and microorganisms is apparently regulated by tryptophan through the feedback inhibition of the enzyme anthranilate synthase (hereinafter referred to as AS). AS is the branchpoint enzyme which catalyzes the conversion of chorismate to anthranilate. AS and the four other enzymes in the pathway have been identified and partially purified from crude extracts of cell cultures of higher plants (Hankins et al., 1976, Plant Physiol. 57: 101-104; Widholm, 1973, Biochim. Biophys. Acta 320: 217-226). However, AS is very unstable and is therefore difficult to purify.

Resistance to Inhibition by Tryptophan Analogs

Tissue culture methods have been used to select for resistance to growth inhibition by amino acid analogs in several plant species. The results of these investigations can be separated into two categories based on whether or not amino acid analog tolerance was stably inherited and expressed in the progeny of plants regenerated from the selected resistant cultures. This criterion clearly establishes the mutant nature of the selected trait.

Microorganisms are able to control tryptophan biosynthesis by feedback inhibition and by end-product repression. The site of action of several growth inhibitory analogs (e.g., 5-methyltryptophan, 4-methyltryptophan, 5-fluorotryptophan, 5-hydroxytryptophan, 7-azatryptophan, 3$\beta$-indoleacrylic acid, 3-methylanthranilic acid) has been extensively studied in microorgansims. Studies with *Escherichia coli* showed that specific enzymes in the pathway could be inhibited by the appropriate analog (Moyed, 1960, J. Biochem. 235:1098; Trudinger and Cohen, 1956, 62:148; Moyed and Friedman, 1958, Science 129:968). Moyed (1960) and Sommerville and Yanofsky (1965, J. Mol. Biol. 11:747) showed that *E. coli* mutants resistant to 5-methyltryptophan could be recovered if the bacteria were grown in growth inhibitory concentrations of 5-methyltryptophan. The AS in several cell lines was found to be less sensitive to inhibition by tryptophan or 5-methyltryptophan due to an altered AS.

Plant cell cultures selected for resistance to amino acid analogs or to certain combinations of amino acids may contain increased levels of the corresponding free amino acid. For example, cultured tobacco, carrot, potato and the weed *Datura inoxia* cell lines have been selected which are resistant to growth inhibition by 5-methyltryptophan (hereinafter referred to as 5MT) through an altered AS as described below.

Widholm (1972, Biochim. Biophys. Acta 261: 44-51) demonstrated that the tryptophan analogs 5-methyltryptophan, 4-methyltryptophan, 5-fluorotryptophan and 6-fluorotryptophan cause growth inhibition of tobacco (*Nicotiana tabacum*) and carrot (*Daucus carota*) cell cultures. This inhibition of growth could be reversed by the addition of anthranilic acid, indole, or L-tryptophan. Anthranilate synthase was determined to be very sensitive to these analogs and the tryptophan analogs inhibited cell growth by limiting tryptophan synthesis through inhibition of anthranilate synthase.

The growth of cultured tobacco cells was inhibited by 5MT, but some tobacco cell lines were resistant to growth inhibitory concentrations of 5MT (Widholm, 1972, Biochim. Biophys. Acta 261:52-58). Resistance was stable for at least 60 cell mass doublings even without selection pressure (i.e., without 5MT). In addition, 5MT resistant cells were resistant to growth inhibition by other tryptophan analogs. Free tryptophan levels increased in 5MT resistant cells about 10-fold over control tissue. The enzyme anthranilate synthase was found to be less sensitive to inhibition by tryptophan or 5MT.

Carrot cell lines that were resistant to growth inhibition by 5MT were also selected by Widholm (1972, Biochim. Biophys. Acta 279:48–57). This characteristic was generally stable in the absence of the tryptophan analog for at least 100 cell doublings. 5MT resistant cells were also resistant to other tryptophan analogs. Cellular free tryptophan concentrations in 5MT resistant cell were substantially increased, 2170 $\mu$M as compared to 81 $\mu$M (27-fold) for control tissue. Anthranilate synthase was shown to be altered in the 5MT resistant cells. The enzyme was about 5-fold less sensitive to inhibition by tryptophan or 5MT.

Singh and Widholm (1975, Biochem. Genet. 13:357–367) described a mutant in corn, Zea mays L., blue fluorescent-1, that possessed increased anthranliate synthase activity which was less sensitive to feedback inhibition. The mutant also accumulated anthranilic acid. In contrast to previous work in tobacco and carrot, however, the altered anthranilate synthase activity did not lead to significant overproduction of tryptophan in mature corn plants or seed.

Carlson and Widholm (1978, Physiol. Plant 44:251–255) obtained potato cell (Solanum tuberosum) cultures resistant to 5MT. Anthranilate synthase was shown to be less sensitive to inhibition by tryptophan or by 5MT. There appeared to be two forms of anthranilate synthase present, one sensitive and one resistant to 5MT. In the selected cell lines the level of resistant AS was greatly increased. The range of free tryptophan concentrations were from 970 to 1400 $\mu$M in selected cultures compared to 29 $\mu$M in control tissues.

Widholm (1980, in Plant Cell Cultures: Results and Perspectives, F. Sala, B. Parisi, R. Cella, O. Ciferri (eds.), Elsevier/North Holland Biomedical Press, Amsterdam, pp. 157–159) described plants regenerated from 5MT resistant N. tabacum suspension cultures. While the cultures had an anthranilate synthase enzyme less sensitive to feedback inhibition by tryptophan and exhibited an increased level of free tryptophan (approximately 25-fold), the leaves of the regenerated plants did not express the altered form of the control enzyme and did not form roots in medium containing 5MT. The resistance trait was, however, expressed in callus derived from the regenerated plant. Thus it appears to be difficult to obtain expression in tobacco of the 5MT resistance selected in cell culture.

Finally, Ranch et al. (1983, Plant Physiol. 71:136–140) selected for 5MT resistance in cell cultures of Datura innoxia, a dicot weed and showed that the resistant cell cultures contained increased tryptophan levels (8 to 30 times higher than the wild type level) and an AS with less sensitivity to tryptophan. Regenerated plants were also resistant to 5MT, contained an alterated AS and had a greater concentration of free tryptophan (4 to 44 times) in the leaves than the control plants. In contrast to the studies with N. tabacum where the altered enzyme was not expressed in plants regenerated from resistant cell lines, these results indicated that the amino acid overproduction phenotype could be selected at the cellular level and expressed in whole plants regenerated from the selected cells in Datura innoxia.

Although it is possible to select for 5MT resistance in certain cell cultures and plants, this characteristic does not necessarily correlate with the overproduction of free amino acid in whole plants. Additionally, plants regenerated from 5MT resistant lines frequently do not express the altered form of the control enzyme. Nor is it expected that this characteristic will be stable over a period of time and be passed along as a heritable trait. Thus, it would be advantageous to obtain plants which produce high levels of tryptophan in mature plants and their seeds and genetically transmit this characteristic to their progeny.

SUMMARY OF THE INVENTION

This invention is directed to novel plant genotypes, and in particular novel genotypes of cereal crops, including maize, rice, wheat, barley, sorghum, oats, rye, and millet which produce increased levels of free tryptophan. As an exemplary embodiment, a new maize genotype is described in the example presented herein which is resistant to inhibition by 5MT at concentrations which normally inhibit growth. The resultant lines overproduce tryptophan in callus culture, tissues, plants and seeds. The present invention utilizes cell culture technology to isolate, characterize and develop plant cell lines, and particularly maize cell lines, which overproduce tryptophan in callus cultures, plant tissues, plants and seeds. Additionally these maize lines genetically transmit this trait to their progeny. This maize genotype may be used for human or animal consumption, or as a source from which tryptophan can be extracted for other purposes.

In addition maize seeds having an endogenous free tryptophan content of between at least 0.2 milligrams per gram dry seed weight and preferably about at least 1 milligram per gram dry seed weight are within the scope of the present invention. For cereal crops generally, the invention includes novel mutant seeds having an endogeneous free tryptophan content of at least ten times that of corresponding non-mutant seeds.

The present invention also provides for the production of a plant cell enzyme which is relatively resistant to inhibition by tryptophan and a tryptophan analog which normally inhibits the activity of this enzyme. This enzyme, an altered anthranilate synthase (AS), confers resistance to inhibition by certain tryptophan analogs and permits growth of callus cultures, plant tissues, plants and seeds in the presence of these same analogs at concentrations which normally inhibit growth before alteration. This invention is also directed to processes and compositions for making and utilizing this altered enzyme, as well as the gene encoding the enzyme.

In summary, for purposes of convenience, the invention can be divided into the following categories for the purpose of description: (a) mutant plant seeds, mutant plant tissue cultures, and mutant plants having an endogenous free tryptophan content of at least ten times the amount of corresponding non-mutant plant seed, plant tissue cultures and plants, wherein the plant may be a monocot and particularly a cereal crop from the group consisting of maize, rice, wheat, barley, sorghum, oats, rye, and millet and the like; (b) mutant maize seeds, mutant maize tissue clutures, mutant maize plants having an endogenous free tryptophan content of at least ten times the amount of corresponding non-mutant maize seeds, maize tissue cultures, an maize plants; and (c) methods for producing tryptophan by extracting tryptophan from (a) and (b).

As regards the specific embodiments of (a) and (b): the seed is capable of germinating into a plant, the plant and plant tissue culture each of which is capable of expressing a gene encoding an altered anthranilate synthase resistant to inhibition by tryptophan or a tryptophan analog at concentrations which normally inhibit the activity of the anthranilate synthase before alteration. The plant seed, and plant tissue culture may tranmsit the gene encoding the altered anthranilate synthase to its progeny, and the gene before alteration may be from a eukaryotic or prokaryotic organism or may be made in whole or part by chemical or enzymatic methods.

It is to be understood that the following detailed description presents a single embodiment of the invention. This particular embodiment relates to novel maize genotypes which allows the production of increased levels of tryptophan.

DETAILED DESCRIPTION OF ONE EMBODIMENT OF THE INVENTION

This embodiment of the present invention relates to novel maize genotypes which produce increased levels of free tryptophan. The novel genotypes are resistant to inhibition by 5MT at concentrations which normally inhibit growth. The resistant lines overproduce tryptophan. Methods and compositions are provided for producing callus cultures, plant tissues, plants and seeds which overproduce tryptophan and genetically transmit this trait to their progeny. Also described are cell culture selection techniques to select for novel maize genotypes resistant to tryptophan analogs and which overproduce tryptophan. The production of these maize lines encompasses isolation, characterization, and development of these maize lines and regeneration of plants from these cultures which are resistant to tryptophan analogs. Additionally, the present invention provides for the production of a plant cell enzyme which is relatively resistant to inhibition by tryptophan and certain tryptophan analogs which normally inhibit the activity of this enzyme. The methods provided in the present invention may also be used to produce increased levels of free tryptophan in monocots and other cereal crops, including but not limited to rice, rye, millet, wheat, barley, sorghum and oats.

The method of this invention may be divided into the following areas for the purposes of description: (1) determination of the appropriate selection conditions; (2) the strategy for selection of 5MT resistant and tryptophan overproducer maize cell lines; (3) selection and characterization of 5MT resistant and tryptophan overproducer cell lines; (4) regeneration of resistant plants and production of seed; and (5) development of 5MT resistant and tryptophan overproducer commercial hybrid seed.

Strategy for Selection of Tryptophan Overproducer Cell Lines

Efficient selection of a desired tryptophan analog resistant, tryptophan overproducer mutant using tissue culture techniques requires careful determination of selection conditions. These conditions are optimized to allow growth and accumulation of tryptophan analog resistant, tryptophan overproducer cells in the culture while inhibiting the growth of the bulk of the cell population. The situation is complicated by the fact that the vitality of individual cells in a population is highly dependent on the vitality of neighboring cells.

Conditions under which cell cultures are exposed to a tryptophan analog are determined by the characteristics of the interaction of the compound with the tissue. Such factors as degree of toxicity and rate of inhibition should be considered. The accumulation of the compounds by cells in culture, and the persistence and stability of the compounds, both in the media and in the cells, also need to be considered. Additionally, it is important to determine whether the effects of the compounds can be readily reversed by addition of tryptophan.

The effects of the analog on culture viability and morphology need to be carefully evaluated. It is especially important to choose analog exposure conditions which have no impact on plant regeneration capability of cultures. Choice of analog exposure conditions is also influenced by whether the analog kills cells or simply inhibits cell divisions.

The choice of a selection protocol is dependent upon the considerations described supra. The protocols briefly described below may be utilized in the selection procedure, although the present invention is not limited to these procedures. In the first protocol, finely divided cells in liquid suspension culture are exposed to high analog levels for brief periods of time. Surviving cells are then allowed to recover and accumulate and are then reexposed for subsequently longer periods of time. Alternatively, organized, partially differentiated cell cultures are grown and subcultured with continuous exposure to initially low analog levels. Analog concentrations are then gradually increased over several subculture intervals.

Selection and Characterization of Resistant Cell Lines

Selections are carried out until cells or tissue are recovered which are observed to be growing well in the presence of normally inhibitory levels of the tryptophan analog. These cell "lines" are subcultured several additional times in the presence of the analog to remove non-resistant sections and then characterized. The amount of resistance which has been obtained is determined by comparing the growth of these cell lines with the growth of unselected cells or tissue in the presence of various analog concentrations. Stability of the resistance trait of the cultured cells may be evaluated by simply growing the selected cell lines in the absence of analog for various periods of time and then analyzing growth after re-exposing the tissue to the analog.

As an alternative method to selection of cultures exposed to increased concentrations of analog on solid medium, cells may be selected in liquid medium and the surviving cells recovered using a feeder layer of healthy cells on solid medium.

The resistant cell lines may also be evaluated using in vitro chemical studies to verify that the site of action of the analog is altered to a form which is less sensitive to inhibition by tryptophan.

Plant Regeneration and Production of Seed

Cell lines exhibiting satisfactory levels of resistance to the tryptophan analog are put through a plant regeneration protocol to obtain mature plants and seed expressing the resistance trait. The plant regeneration protocol allows the development of somatic embryos and the subsequent growth of roots and shoots.

Mature plants are then obtained from cell lines that are known to express the trait. If possible, the regenerated plants are self pollinated. In addition pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Development of Tryptophan Overproducer Commercial Hybrid Seed

The commercial value of tryptophan overproducer corn is greatest if many different hybrid combinations are available for sale. The farmer typically grows more than one kind of hybrid based on such differences as maturity, standability or other agronomic traits. Additionally, hybrids adapted to one part of the corn belt are not adapted to another part because of differences in such traits as maturity, disease and insect resistance. Because of this, it is necessary to breed tryptophan overproduction into a large number of parental lines so that many hybrid combinations can be produced.

Adding the tryptophan overproduction genotype to agronomically elite lines is most efficiently accomplished if the genetic control of analog resistance and tryptophan overproduction is understood. This requires crossing tryptophan overproducer plants with sensitive plants and studying the pattern of inheritance in segregating generations to ascertain whether the trait is expressed as a dominant or recessive, the number of genes involved, and any possible interaction between genes if more than one are required for expression. This genetic analysis can be part of the initial efforts to convert agronomically elite, yet sensitive, lines to resistant lines.

A conversion process (backcrossing) is carried out by crossing the original overproducer line to normal elite lines and crossing the progeny back to the normal parent. The progeny from this cross will segregate such that some plants carry the gene responsible for overproduction whereas some do not. Plants carrying such genes will be crossed again to the normal parent resulting in progeny which segregate for overproduction and normal production once more. This is repeated until the original normal parent has been converted to an overproducing line, yet possesses all other important attributes as originally found in the normal parent. A separate backcrossing program is implemented for every elite line that is to be converted to tryptophan overproducer line.

Subsequent to the backcrossing, the new overproducer lines and the appropriate combinations of lines which make good commercial hybrids are evaluated for overproduction as well as a battery of important agronomic traits. Overproducer lines and hybrids are produced which are true to type of the original normal lines and hybrids. This requires evaluation under a range of environmental conditions where the lines or hybrids will generally be grown commercially. For production of high tryptophan corn it may be necessary that both parents of the hybrid seed corn be homozygous for the high tryptophan character. Parental lines of hybrids that perform satisfactorily are increased and used for hybrid production using standard hybrid seed corn production practices.

Alternate Methods of Obtaining Tryptophan Overproducer Mutants

Any method which can be utilized to improve the quality and quantity of free tryptophan in plants can be utilized. Generally, biosynthesis of amino acids, including tryptophan, are controlled by feedback regulation. The two major types of feedback regulation are feedback (or end product) inhibition and feedback repression. In feedback inhibition, the final metabolite of the pathway inhibits the activity of an enzyme of the pathway. Feedback repression is the inhibition of formation of one or more enzymes in a pathway by an end product or a derivative of the end product. For many amino acid biosynthetic pathways the amino acid end product first combines with its transfer RNA (tRNA) to cause repression. Feedback regulation may be circumvented by (a) decrease in the concentration of an inhibitory or repressive end product or (b) mutational alteration of the enzyme or enzyme forming system to a condition less sensitive to feedback effects, i.e., mutation to feedback resistance. (For a more complete review of this topic see Demain, 1971, Advan. Biochem. Eng. 1:113–141.)

In the embodiment of the present invention mutants are isolated that may possess an enzyme resistant to feedback inhibition and/or feedback repression by using analogs of the amino acid that exert inhibition and/or repression but cannot be used for protein synthesis. Mutants may be resistant to the analog due to an alteration in the structure of the feedback-inhibited enzyme (inhibition resistant) whereas others may have an altered enzyme-forming system (repression resistant). Additionally, these mutants overproduce the amino acid due to altered control mechansms. Mutations to both types of resistance (double mutants) in one line may result in a marked increase in amino acid production.

Any alteration or replacement of AS which leads to feedback regulation and overproduction of tryptophan in callus culture, tissue culture, seed and regenerated plants may be utilized in this embodiment of the present invention. AS may be altered or replaced in any plant species; of especially great importance are the agronomic and horticulture crops which are normally deficient or produce low quantities of tryptophan. The alteration of AS may be accomplished by any of a variety of means, including but not limited to the following methods: (1) spontaneous variation and direct mutant selection in tissue cultures; (2) direct or indirect mutagenesis procedures on tissue cultures of all types, seeds and plants; and (3) isolation of genes, manipulation, modification, or synthesis in whole or part of genes using molecular biology, chemical technologies and state-of-the-art procedures and reintroduction of resistance genes into plants.

Additionally, any type of AS modification which leads to a change in regulatory elements, or resistance to, or tolerance of, chemical compounds applied to plants may be utilized. These changes may include alterations in enzyme structure and changes in enzyme expression and/or function. Tryptophan overproducers may also be obtained by gene mutations (e.g., single or multiple site mutations, or the presence of multiple gene copies of the enzyme), derepression of the enzyme, replacement or supplementation (i.e., gene therapy or the addition of extra genes), by any means, of an endogenous AS with any other AS from another source, including but not limited to prokaryotic or eukaryotic organisms or by chemical synthesis of a gene that catalyzes the same reactions as AS.

Genes encoding AS are common to the tryptophan and branched chain amino acid pathways in plants and microorganisms (Umbarger, 1978, Ann. Rev. Biochem. 47: 533–606). In higher plants, the biosynthesis of L-tryptophan has been shown to be controlled by feedback inhibition of AS by the end product, tryptophan (Carlson and Widholm, 1978, Physiol. Plant 44:251–255). AS genes with a variety of regulatory characteristics are available from a variety of bacterial mutants.

An important aim of traditional plant breeding is to engineer improved plants that are valuable as crop plants and serve as a source of nutritionally valuable proteins, as biomass or as sources of pharmaceuticals and enzymes. Present day genetic engineering techniques are geared towards similar goals.

To introduce isolated genes or a group of genes into the genome of plant cells an efficient host gene vector system is necessary. The foreign genes should be expressed in the transformed plant cells and stably transmitted (somatically and sexually) to the next generation of cells produced. The vector should be capable of introducing, maintaining and expressing a gene in plant cells, from a variety of sources, including but not limited to plants and animals, bacteria, fungi, yeast or virus. Additionally it should be possible to introduce the vector into a wide variety of plants. The location of the new gene in the plant genome may be important in determining effective gene expression of the genetically engineered plant. In addition, to be effective, the new gene must be passed on to progeny by normal breeding.

Directed genetic modification and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens*. Using recombinant DNA techniques and bacterial genetics, any foreign piece of DNA can be inserted into T-DNA in Agrobacterium. Following infection by the bacterium or Ti plasmid, the foreign DNA is inserted into the host plant chromosomes, thus producing a genetically engineered cell and eventually a genetically engineered plant. A second approach is to introduce root-inducing (Ri) plasmids as the gene vectors. While Agrobacterium appear to attack only dicots, many important crop plants including corn, wheat, rice, barley, oats, sorghum, millet, and rye are monocots and are not known to be susceptible to transformation by Agrobacterium.

The Ti plasmid, however, may be manipulated in the future to act as a vector for monocot plants. Additionally, using the Ti plasmid as a model system it may be possible to artificially construct gene vectors for monocot plants.

Ti-plasmids might also be introduced into monocots by artificial methods such as microinjection, or fusion between monocot protoplasts and bacterial spheroplasts containing the T-region which can then be integrated into the plant nuclear DNA.

Genetic engineering of plants may also be accomplished by introducing the desired DNA containing functional genes which will result in high levels of free tryptophan, or high levels of an intermediate in the tryptophan biosynthetic pathway which are less sensitive to feedback inhibition into plant tissues or cells using DNA molecules of a variety of forms and origins including, but not limited to: plant pathogens such as DNA viruses like Cauliflower Mosaic virus (CaMV) or geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants).

The Cauliflower Mosaic virus (CaMV) has a gene the function of which is to prevent certain insects from destroying the virus. The remaining parts of the gene are redundant and can be replaced witn a gene(s) which is useful to the plant breeder. The geminiviruses (or twin viruses) which are imposed of two strands of DNA wrapped up in twin capsules of proteins can be used to transfer foreign genes into monocot plants. Transposons may also be used to carry foreign genes into plant DNA.

DNA containing AS genes may be delivered into the plant cells or tissues directly by infectious plasmids, such as Ti, viruses or microorganisms like *A. tumefaciens*, the use of liposomes, microinjection by mechanical or laser beam methods, by whole chromosomes or chromosome fragments, and by direct spraying of an infectious plant virus on crops.

Tryptophan overproducer mutants may also be developed using any of the methods described supra and also other means including, but not limited to, conventional genetic and plant breeding procedures, whole plant genetic methods and somatic hybridization by protoplast fusion.

Commercial Approaches to Tryptophan Extraction from High Tryptophan Maize Seed

There are a number of methods that could be used to extract the free tryptophan from high tryptophan corn, however, the more economical of these would likely involve extracting the tryptophan prior to or following standard wet or dry milling processes (Watson, 1977 in Corn and Corn Improvement, G. F. Sprague (ed.), Amer. Soc. of Agronomy, Madison, Wisc.). This permits the value of the tryptophan to be added to the value of milled products.

In the wet milling process, one of the initial steps involves treating the kernels with an acidic aqueous solution and allowing a limited amount of lactic acid fermentation to occur. This treatment conditions and softens the kernel and solubilizes many small molecules in the kernel including free amino acids. This acid environment will, however, result in breakdown of most of the solubilized tryptophan. Thus, to obtain significant amounts of this commodity, it will be necessary to extract the tryptophan prior to the acid treatment step. A method that can be used to carry out this pre-extraction process is described below.

Maize seed can be processed in a series of vats at elevated temperatures (approximately 150° F.) in an aqueous environment at basic/neutral pH (pH≦10). Water is added to the corn that has been extracted the longest in the process and flows in a countercurrent manner towards the newly introduced seed. Following several days of extraction the corn is then transferred to a standard wet milling plant. The liquid from the extraction process can then be filtered to remove solids then treated by standard chemical means, solvent extraction/phase separation, ion exchange chromatography and crystallization, to concentrate and purify the tryptophan. The degree of purification will depend on the type of product desired—feed supplement, chemical feed stock, reagent chemical, etc.

In the dry milling processes corn kernels are cleaned, brought to 20-22% moisture then milled, pressed and sorted to give a variety of fractions—hominy feed, flaking, medium and fine grits, meal and flour. One or more of these fractions can then be extracted with water under neutral to basic conditions at elevated temperature to obtain the tryptophan. Again, the tryptophan can then be concentrated and purified by standard chemical methods including solvent extraction/phase separation, ion exchange chromotography and crystalization.

Tryptophan may also be recovered by other conventional procedures. For example, a method for recovery is presented in U.S. Pat. No. 3,759,790 which is hereby incorporated by reference into the present specification.

EXAMPLES

According to one particular embodiment of the present invention, maize tissue cultures resistant to 5MT were selected and plants which were resistant to the tryptophan analog were regenerated from these cultures. The selected resistant line has a greatly increased level of free tryptophan. A detailed description of the invention is presented in the subsections below.

Characterization of the Effects of 5-Methyltryptophan and Strategy for Selection of Resistant Maize Cells Initiation and Maintenance of Maize Cell Cultures Which Retain Plant Regeneration Capacity Friable, embryogenic maize callus cultures were initiated from hybrid immature embryos produced by pollination of inbred line A188 plants (University of Minnesota, Crop Improvement Association) with pollen of Inbred line B73 plants (Iowa State University). Ears were harvested when embryos had reached a length of 1.5 to 2.0 mm. The whole ear was surface sterilized in 50 v/v commercial bleach (2.63% w/v sodium hypochlorite) for 20 minutes at room temperature. The ears were then washed with sterile distilled, deionized water. Immature embryos were aseptically isolated and placed on nutrient agar initiation/maintenance media with the root/shoot axis exposed to the media. Initiation/maintenance media consisted of N6 basal media (Chih-ching in Proceedings of Symposium on Plant Tissue Culture, May 25-30, 1978, Science Press, Peking, pp. 43-50) with 2% (w/v) sucrose, 1.5 mg per liter 2,4-dichlorophenoxyacetic acid (2,4-D), 6 mM proline, and 0.9% (w/v) agar.

The immature embryos were incubated at 26° C. in the dark. Cell proliferations from the scutellum of the immature embryos were evaluated for friable consistency and the presence of well defined somatic embryos. Tissue with this morphology was transferred to fresh media 10 to 14 days after the initial plating of the immature embryos. The tissue was then subcultured on a routine basis every 12 to 16 days. Sixty to eighty milligram quantities of tissue were removed from pieces of tissue that had reached a size of approximately one gram and transferred to fresh media. Subculturing always involved careful visual monitoring to be sure that only tissue of the correct morphology was maintained. The presence of the somatic embryos ensured that the cultures would give rise to plants under the proper conditions.

Callus Culture Growth Inhibition by 5-Methyltryptophan

The tryptophan analog, 5-methyltryptophan (5MT), was used for selection of tryptophan overproducer mutants as discussion in Section 5 supra. The effect of various concentrations of 5MT on callus growth on solid media was determined. Quantities of tissue averaging 50 mg in size were transferred to nutrient agar maintenance media containing 5MT concentrations ranging from 1.0 to 200 μM. Four tissue pieces were placed on each plate with four plates per analog concentration. After 28 days growth, the tissue was weighed again. Inhibition of growth rate was found to be half maximal in the 3 to 10 μM 5MT range of concentration. Cell death was observed at analog concentrations of 100 and 200 μM. Tryptophan was shown to reverse all the growth inhibitory effects of 5MT.

Selection and Characterization of a 5-Methyltryptophan Resistant Cell Line

The selection protocol used to identify and isolate analog resistant cells was formulated to take into account that: (1) the effects of the 5MT were reversible and (2) the effects of the analog increased over time. Therefore, the procedure involved exposing tissue continuously to a moderate 5MT concentration over several subculture intervals and keeping careful records of the growth of all tissue in the selection. In this way the analog was allowed to take effect slowly with continuous selection pressure permitting analog tolerant cells to accumulate over time and yet not affect the potential for plant regeneration. This procedure allowed for the selection of cells with even low levels of 5MT tolerance (2- to 3-fold in analog concentration).

Selection of 5-Methyltryptophan Resistant Cell Line

Many selections were carried out utilizing the selection protocol described supra. The selection of one such 5MT resistant line that was identitied and characterized is described below in detail.

Approximately three grams of vigorously growing maize callus tissue was transferred to maintenance media in petri plates containing 33 μM 5MT. Plates were prepared and individual tissue weighing 30 to 40 mg were plated on each plate in groups of 10. The 5MT level was chosen from growth inhibition studies to provide less than from about 20% to about 40% of normal growth during the first four weeks of analog exposure.

Surviving tissue sectors showing some growth and retention of embryogenic morphology (i.e., presence of somatic embryos) during the first 8 weeks of growth were subcultured on fresh media containing 33 μM 5MT. Each piece of tissue was labeled and became the progenitor of a "line." A complete genealogy was maintained and recorded for future subcultures. Subsequent subculture intervals ranged from 15 to 30 days depending on overall growth of the callus tissue.

Figure 1:
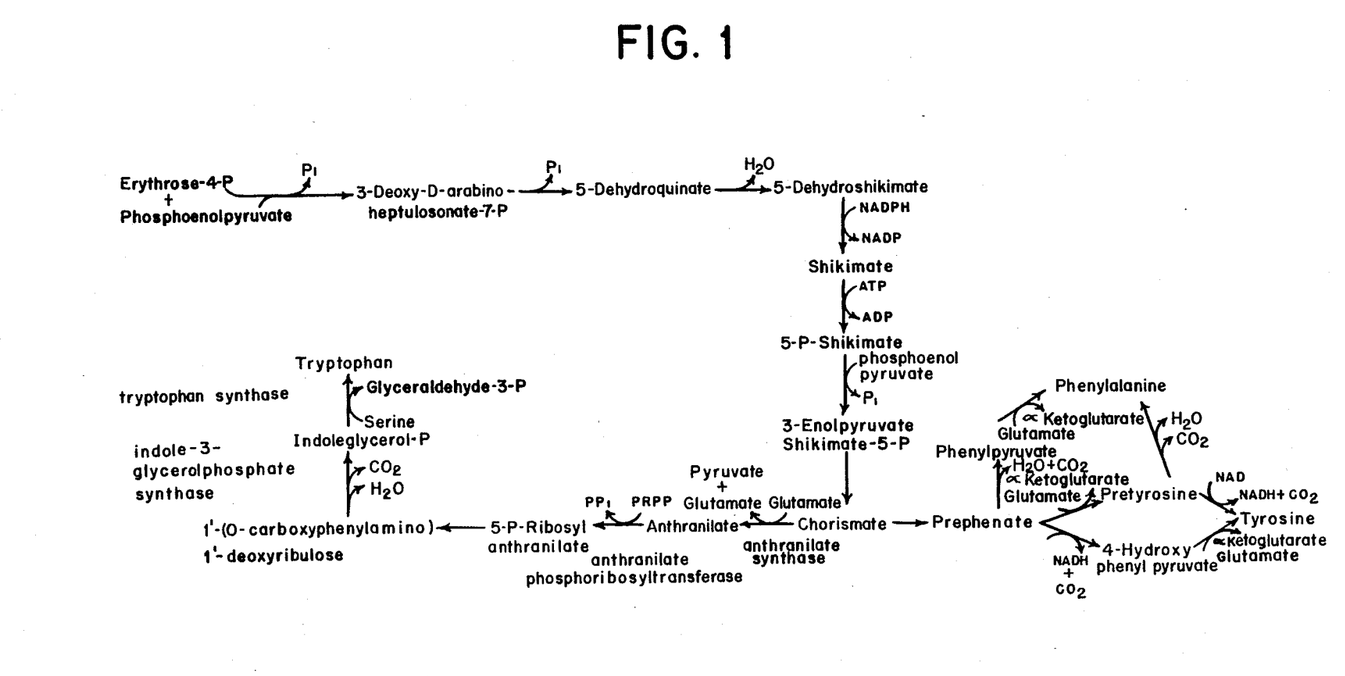
FIG. 1 shows the biosynthetic pathway for tryptophan and the other aromatic amino acids in plants.
Figure 2:
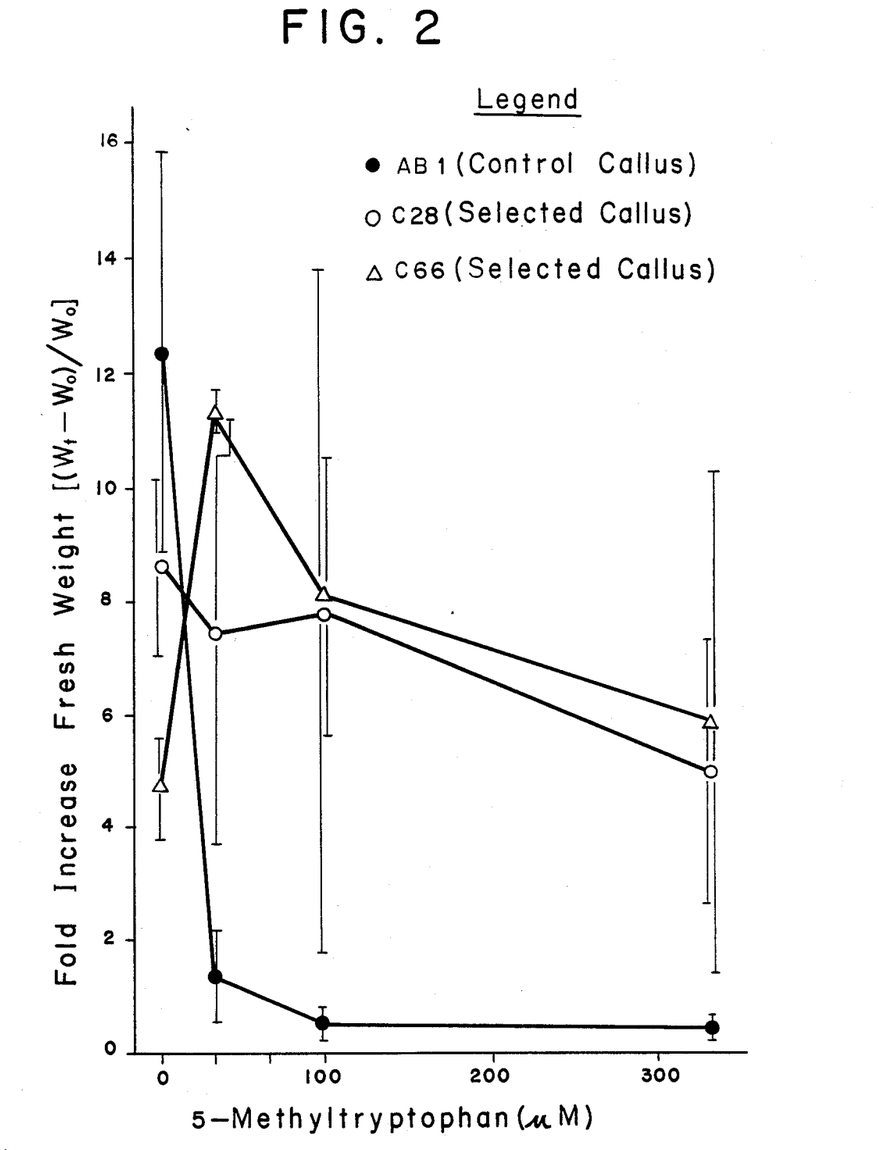
FIG. 2 diagrammatically shows the growth inhibition for mutant callus lines C28 and C66 and for parental line AB1. The increased fresh weight of tissue is shown for varying concentrations of 5-methyltryptophan.

For each transfer all tissue showing growth and somatic embryo forming ability were placed on fresh media. At the third transfer, the concentration of 5MT was increased to 100 μM. During the course of the selection process, the total number of lines decreased as the analog mediated growth inhibition became more intense. Two lines however, increased in size and by the end of the fourth month of selection were identified as resistant to 5MT. These cell lines were identified as maize line C28 and C66. Growth inhibition studies showed that growth was no longer seriously inhibited by the presence of the analog at 100 μM or below compared to the parental cell line AB1 as shown in FIG. 2. Throughout this selection process, the selected cell lines maintained a friable appearance that was similar to the appearance of the original parent cell line.

Characterization of Maize Cell Line C28

The resistant cell line was characterized to evaluate: (1) the magnitude of the resistance; (2) the stability of the resistance trait; and (3) the level of free tryptophan. In addition the sensitivity of the enzyme anthranilate synthase to 5MT was measured.

Four week growth inhibition studies were carried out with 5MT as described supra. The level of 5MT giving 50% growth inhibition was determined to be between 300 and 400 μM for the C28 line compared to 3 to 10 μM for unselected parent tissue. Stability of the resistance trait was examined by growing the C28 line on maintenance medium without 5MT. Periodically these cultures were retested for resistance to the analog. Cultures were shown to be 5MT resistant without selection pressure for greater than 10 months.

Analysis of Free Trytophan

Free tryptophan levels in tissue cultures of line C28 was determined by amino acid analysis. Tissue cultures were grown without 5MT for a minimum of 2 weeks and then 1 gram fresh weight quantities of callus tissue were ground with sand with a mortar and pestle in 1 ml of 12:5:3 methanol:chloroform:water (MCW). One ml of MCW was added and the extract centrifuged at 10,000×g for 10 minutes. The pellet was reextracted with 2 ml MCW, the supernatants combined and 1 ml each of chloroform and water was added. The aqueous phase was then subjected to cation exchange chromatography. These extracts were passed through Bond Elut SCX columns (Analytichem International Inc., Harbor City, Calif.) which had been equilibrated with 10 ml 1 N HCl then 10 ml water. Following sample application the columns were washed witn 5 ml distilled, deionized water, and the amino acids were eluted with 2 ml aliquots of 5% v/v triethylamine. The aliquots were combined (6 ml) and lyophilized. Free amino acid levels were determined by using reverse phase high performance liquid chromatography following pre-column derivatization with o-phthalidialdehyde (Jones et al., 1981, J. Liq. Chromatogr. 4:565–586). The C28 line was shown to contain 78 μg of free tryptophan per gram fresh weight calli while control tissues contained only 4.0 μg per gram fresh weight. (Callus tissue is approximately 90% water, thus on a dry weight basis the C28 line is approximately 780 μg of free tryptophan per gram and ree tryptophan.)

Anthranilate Synthase Assays

Assays were conducted to determine whether 5MT resistance was conferred by an alteration in the gene that codes for the anthranilate synthase enzyme. Crude enzyme extract of AB108 control callus and the selected K17 line of C28 callus were prepared as described below. The K17 line of C28 was derived from a regenerated C28 plant crossed with a control plant and then self-pollinated. Immature embryos were then cultured and a callus line developed as described previously.

Plant callus tissue was ground using a mortar and pestle and extracted with 0.2 M Tris-HCl, pH 8.2, 60% glycerol, 0.2 mM dithiothreitol (DTT), 0.2 mM ethylenediaminetetraacetic acid (EDTA), 1.0 mM magnesium sulfate ($MgSO_4$), 20 mM sodium chloride (NaCl) and 1.0 mM L-tryptophan. One ml extraction buffer was used per 2 g callus. The extract was centrifuged at 10,000×g for 25 minutes at 4° C. The supernatant was applied to a 3 cm×15 cm Bio Gel-P6 column (Bio-Rad, Richmond, Calif.) equilibrated with 0.1 M Tris-HCl, pH 7.6, 10% glycerol, 0.1 mM DTT and 0.1 mM EDTA and eluted with the same buffer. 0.75 ml fractions were collected and fractions containing protein were pooled. The volume of crude extract approximated the volume of supernatant applied to the column. All of the above steps were conducted at 4° C.

Assays were conducted in 1 ml volumes as follows. 50 μl aliquots of extract were assayed at 30° C. for 30 minutes in the presence of 0.25 mM chorismate (barium salt form), 20 mM L-glutamine, 4 mM $MgSO_4$, and $0-10^3$ M 5MT as enzyme inhibitor. The reaction was terminated by the addition of 0.1 ml 2 N acetic acid. The anthranilate was extracted into 2 ml ethyl acetate, vortexed well and centrifuged at 5,000×g for 5 minutes. One ml of the ethyl acetate layer was removed and added to 2.5 ml ethyl acetate and vortexed. The fluorescence due to the production of anthranilate was measured in the 3.5 ml extractant using a Kratos FS950 fluorimeter (Kratos Analytical Instruments, Ramsey, N.J.). The excitation filter used was a 254 nm interference type filter and the emission filter had a 370 nm cutoff point.

Figure 4:
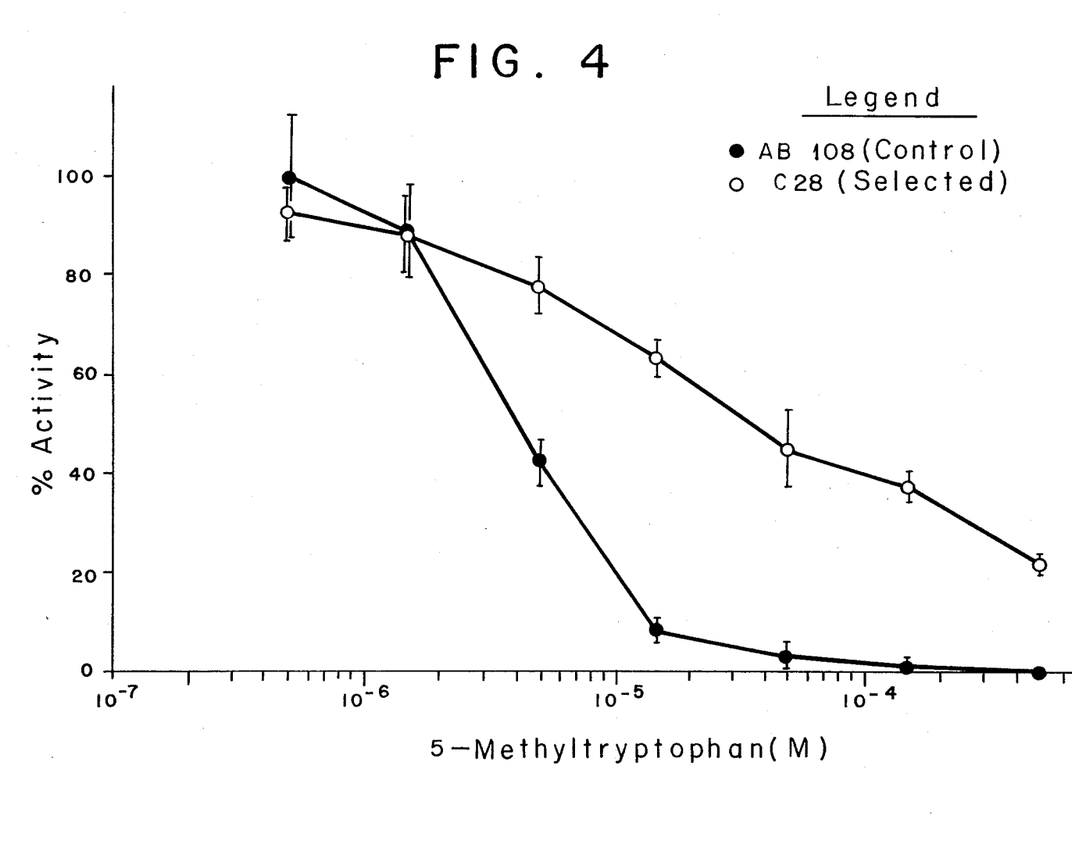
FIG. 4 diagramatically shows the inhibition curve of AS activity for both the control AB108 callus extract and the selected K17 line of C28.

The results of the AS assay of both AB108 callus extract and the selected C28 line are shown in FIG. 4. The C28 derived AS was clearly more resistant to inhibition by 5MT than the control AS. A 10-fold higher 5MT level was needed for 50% inhioition of the C28 compared with the control.

Plant Regeneration and Production of Seed

Plant Regeneration Protocol

Eighty to 90 mg quantities of maize callus tissue were transferred to embryo and shoot development (regeneration) media in petri plates. The media consisted of MS basal media (Murashige and Skoog, 1962, Physiol. Plant 15:473) supplemented with 0.1 mg per liter 2,4-D and $1×10^{-7}$ abscissic acid. 0.25% Gelrite (Kelco Co., San Diego, Calif.) was used as a solid support in place of agar. The tissue was incubated in the dark at 26° C. for one week. The plates were then transferred to a light regime at 26° C. (approximately 300 footcandles, soft white fluorescent) on a cycle of 14 hours light, 10 hours dark. Developing plants reaching a size of 1-3 cm were then transferred to flasks or jars, containing MS media with no supplementation, for further development. When plants reached the two to three leaf stage, they were moved to pots containing vermiculite and exposed to light at 2600 footcandles. These plants were watered with 10 mM $KNO_3$ for one week and then with water until they grew stably. The plants were then transferred to soil for growth to maturity under 4000 footcandles of light for 14 hours.

Mature C28 plants were self pollinated and/or crossed with inbred line A188 (University of Minnesota, Crop Improvement Association) and B73 (Iowa State University) plants. Seed set varied from 6 to over 300 seeds per ear on the 20 self or cross pollinations made.

Characterization Of Progeny Plants and Seeds

Resistance to 5MT in progeny seed was determined by germinating mature embryos on medium containing 100 μM 5MT. Seeds from regenerated self or cross pollinated plants were surface sterilized for 20 minutes in 2.5% sodium hypochlorite, rinsed in sterile water 2 times and soaked overnight in sterile water containing 50 mg/l captan. Mature embryos were cut from the seeds and placed on 0.9% agar medium containing MS salts and 0 or 100 μM 5MT. The mature embryos were germinated under 200-400 footcandle light 14 hour days. After 6 days root and shoot lengths were measured.

Figure 3:
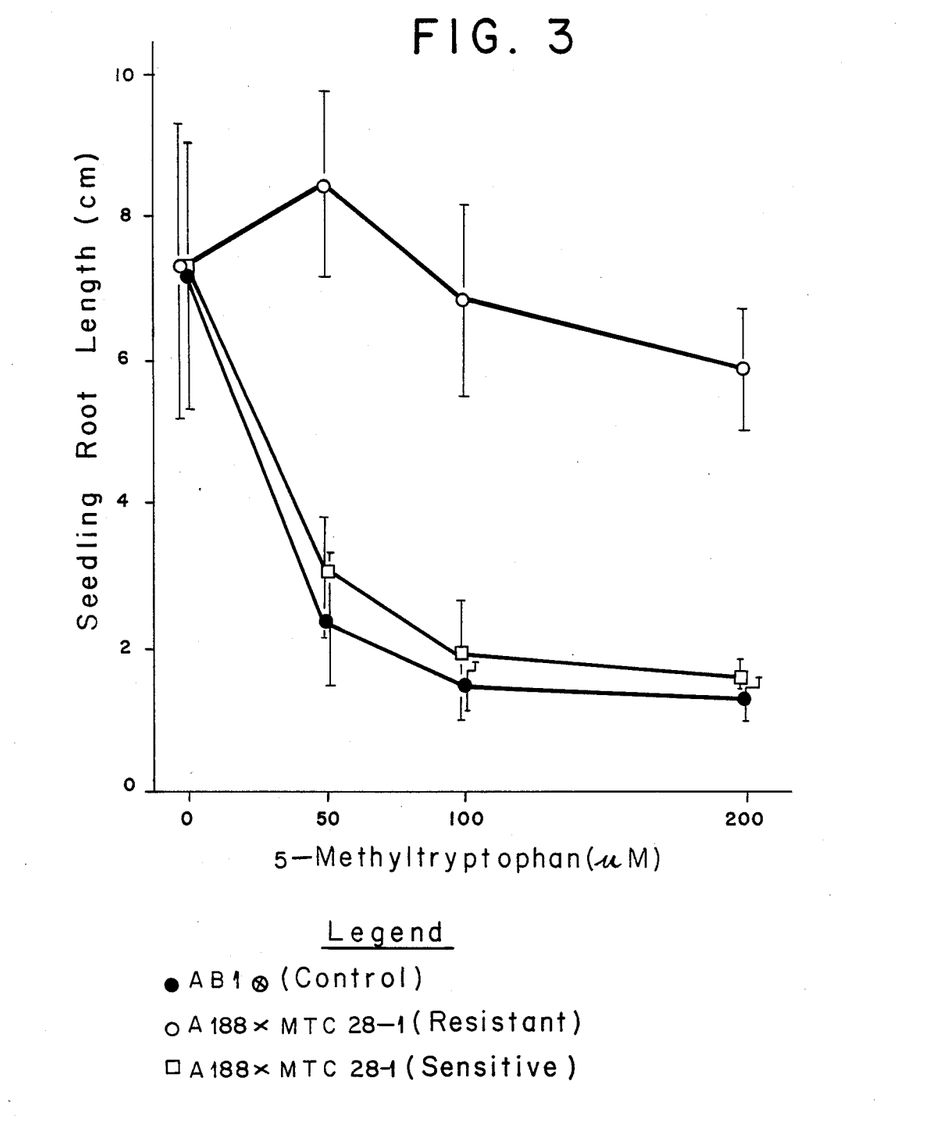
FIG. 3 diagrammatically shows the root length growth responses of seedlings to varying concentrations of 5-methyltryptophan.

C28 progeny seeds responded significantly different than control seeds in this germination assay. In the first generation progeny individual seedlings from the C28 line gave growth responses that could easily be separable into 2 classes as seen in FIG. 3. One group was inhibited 5MT in shoot and root length similar to that observed with control seedlings. A second class showed relative little inhibition by 5MT and growth similar to that observed when seedling were grown without the analog. In tests of seed from self pollinated regenerate C28 plants, the response was 79% long roots (classified resistant) and 21% short roots (classified sensitive) for the 66 seeds tested. In cross pollinated C28 plants the progeny response was 47% resistant and 53% sensitive from a total of 70 seeds.

Seedlings designated resistant were grown to maturity and self pollinated. The progeny from this second generation were also screened as described above. It was shown that resistant plants gave rise to resistant progeny in the 5MT seedling assay.

These results indicated that 5MT resistance selected in cell culture in the line C28 is meiotically transmissable as a dominant character and behaves as would be expected from a trait encoded by a single nuclear gene.

Analysis of Free Tryptophan

Seedling shoot tissues were obtained from seeds germinated in vermiculite at 26° C. in the dark. Fourteen day etiolated shoots were ground individually in 12:5:3 methanol:chloroform:water in a Polytron (Brinkmann Instrument Co., Westbury, N.Y.). Seed samples were prepared by grinding in a Wig-L-bug (Cresent Dental Mfg. Co., St. Lyons, Ill.). Extraction and analysis of free amino acids was performed as described supra for extraction and analysis of free amino acids from callus.

Figure 5:
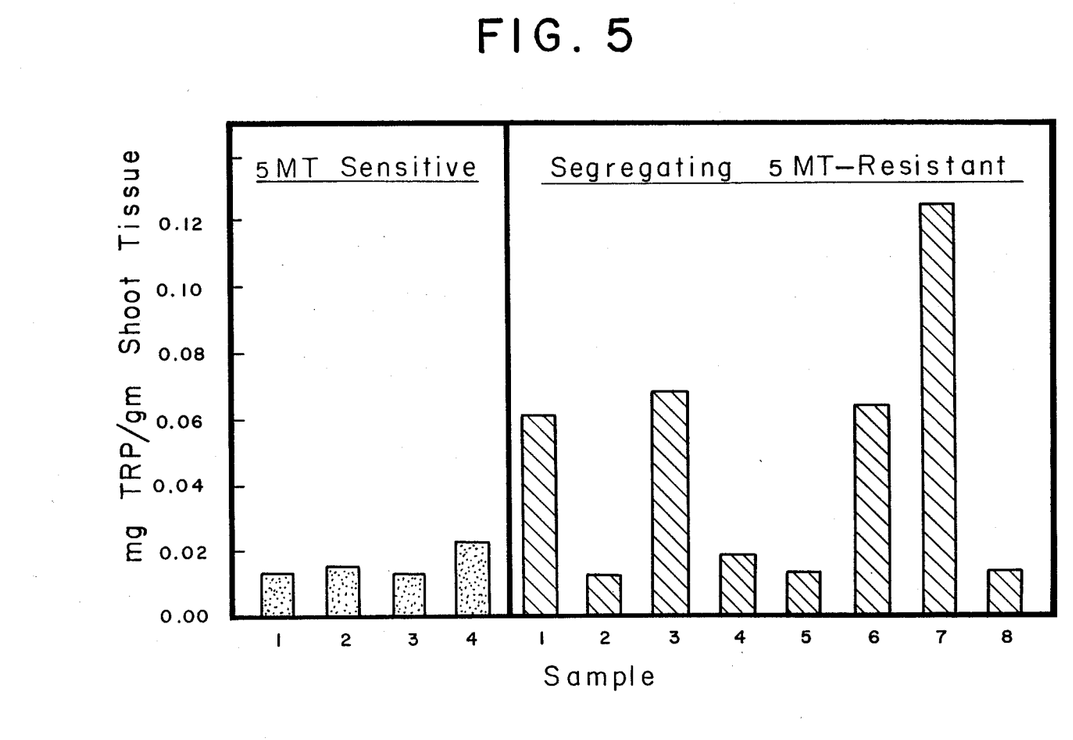
FIG. 5 is a graph of free tryptophan levels in individual seedling shoot tissues examined from a 5MT sensitive population and a population segregating for resistance to 5MT.

The free tryptophan in individual seedling shoots was examined from a population sensitive of 5MT and in a population segregating for resistance to 5MT. The results shown in FIG. 5 indicated a generally lower level of tryptophan in 5MT sensitive seedling than in the segregating resistant population. In the resistant population there were individual seedlings with considerably more tryptophan than found in the sensitive group, as would be expected in a segregating population.

Analyses of one C28 cob that was shown to be homozygous for 5MT resistance indicated that the free tryptophan level was 2.2 mg per gram seed whereas the control was 0.01 mg per gram seed. Indeed maize seed having an endogenous free tryptophan content of between at least about 0.1 mg per gram dry seed weight and preferably at least about 5 mg per gram dry seed weight are within the scope of this invention. This demonstrates that tryptophan analog selections in callus culture can give rise to callus plant shoots and eventually seed with substantially increased levels of free tryptophan.

DEPOSIT OF SEEDS

A collection of seeds, identified as C-28 (2.18-2.21-83), as described herein, has been deposited with In Vitro International, Inc. Ann Arbor, Mich., and has been assigned accession IVI No. 10010.

The present invention is not to be limited in scope by the cell line or seeds deposited, since the deposited embodiments are intended as single illustrations of one aspect of the invention and any cell lines or seeds which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A maize seed having an endogenious free tryptophan content of at least about one-tenth milligram per gram dry seed weight and capable of germinating into a plant capable of producing seed having an endogenous free tryptophan content of at least about one-tenth milligram per gram dry seed weight.

2. The maize seed according to claim 1, having an endogenous free tryptophan content of at least about one milligram per gram dry seed weight and capable of germinating into a plant capable of producing seed having an endogenous free tryptophan content of at least about one milligram per gram dry seed weight.

3. A tryptophan overproducing maize seed capable of germinating into a plant capable of expressing a gene coding for an anthranilate synthase which retains from about 60 to about 80 percent of its activity in the presence of 5-methyltryptophan at a concentration of about $10^{-5}$ M, wherein the plant is capable of transmitting the gene encoding the anthranilate synthase to its progeny.

4. A tryptophan overproducing maize seed having an embryo capable of producing in the presence of 5-methyltryptophan at a concentration of $10^{-4}$ M roots of at least about 60 percent of the length of roots produced in the absence of 5-methyltryptophan, as measured after six days incubation, wherein the seed is capable of germinating into a plant capable of producing seed having an embryo capable of producing in the presence of 5-methyltryptophan at a concentration of $10^{-4}$ M roots of at least about 60 percent of the length of roots produced in the absence of 5-methyltryptopha,n, as measured after six days incubation.

5. A maize seed deposited with In Vitro International, Inc. and assigned IVI accession No. 10010.

6. A maize seed resulting from crossing C-28 with another maize line.

7. A hybrid maize seed having an endogenous free tryptophan content of at least about one-tenth milligram per gram dry seed weight and capable of germinating into a plant capable of producing seed having an endogenous free tryptophan content of at least about one-tenth milligram per gram dry seed weight.

8. The hybrid mazie seed according to claim 7, having an endogenous free tryptophan content of at least about one milligram per gram dry seed weight and capable of germinating into a plant capable of producing seed having an endogenous free tryptophan content of at least about one milligram per gram dry seed weight.

9. A tryptophan overproducing hybrid maize seed capable of germinating into a plant capable of expressing a gene coding for an anthranilate synthase which retains from about 60 to about 80 percent of its activity in the presence of 5-methyltryptophan at a concentration of about $10^{-5}$ M, wherein the plant is capable of transmitting the gene encoding the anthranilate synthase to its progeny.

10. A tryptophan overproducing hybrid maize seed having an embryo capable of producing in the presence of 5-methyltryptophan at a concentration of $10^{-4}$ M roots of at least about 60 percent of the length of roots produced in the absence of 5-methyltryptophan, as measured after six days incubation, wherein the seed is capable of germinating into a plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation.

11. A maize plant capable of producing seed having an endogenous free tryptophan content of at least about one-tenth milligram per gram dry seed weight, wherein the seed is capable of germinating into a plant capable of producing seed having an endogenous free tryptophan content of at least about one-tenth milligram per gram dry seed weight.

12. The maize plant according to claim 11, wherein the plant is capable of producing seed having an endogenous free tryptophan content of at least about one milligram per gram dry seed weight, wherein the seed is capable of germinating into a plant capable of producing seed having an endogenous free tryptophan content of at least about one milligram per gram dry seed weight.

13. A tryptophan overproducing maize plant capable of expressing a gene coding for an anthranilate synthase which retains from about 60 to about 80 percent of its activity in the presence of 5-methyltryptophan at a concentration of about $10^{-5}$ M, wherein the plant is capable of transmitting the gene encoding the anthranilate synthase to its progeny.

14. A tryptophan overproducing maize plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation, wherein the seed is capable of germinating into a plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation.

15. A maize plant derived from seeds deposited with In Vitro International, Inc. and assigned IVI accession No. 10010.

16. A maize plant having an average endogenous free tryptophan content of at least about 0.04 milligrams per gram fresh weight.

17. The maize plant according to claim 16, having an average endogenous free tryptophan content of at least about one-tenth milligram per gram fresh weight.

18. A hybrid maize plant capable of producing seed having an endogenous free tryptophan content of at least about one-tenth milligram per gram dry seed weight, wherein the seed is capable of germinating into a plant capable of producing seed having an endogenous free tryptophan content of at least about one-tenth milligram per gram dry seed weight.

19. The hybrid maize plant according to claim 18, wherein the plant is capable of producing seed having an endogenous free tryptophan content of at least about one milligram per gram dry seed weight, wherein the seed is capable of germinating into a plant capable of producing seed having an endogenous free tryptophan content of at least about one milligram per gram dry seed weight.

20. A tryptophan overproducing hybrid maize plant capable of expressing a gene coding for an anthranilate synthase which retains from about 60 to about 80 percent of its activity in the presence of 5-methyltryptophan at a concentration of about $10^{-5}$ M, wherein the plant is capable of transmitting the gene encoding the anthranilate synthase to its progeny.

21. A tryptophan overproducing hybrid maize plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation, wherein the seed is capable of germinating into a plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation.

22. A maize tissue culture capable of generating a plant capable of producing seed having an endogenous free tryptophan content of at least about one-tenth milligram per gram dry seed weight, wherein the seed is capable of germinating into a plant capable of producing seed having an endogenous free tryptophan content of at least about one-tenth milligram per gram dry seed weight.

23. The maize tissue culture according to claim 22, wherein the plant is capable of producing seed having an endogenous free tryptophan content of at least about one milligram per gram dry seed weight, wherein the seed is capable of germinating into a plant capable of producing seed having an endogenous free tryptophan content of at least about one milligram per gram dry seed weight.

24. A tryptophan overproducing maize tissue culture capable of generating a plant capable of expressing a gene coding for an anthranilate synthase which retains from about 60 to about 80 percent of its activity in the presence of 5-methyltryptophan at a concentration of about $10^{-5}$ M, wherein the plant is capable of transmitting the gene encoding the anthranilate synthase to its progeny.

25. A tryptophan overproducing maize tissue culture capable of generating a plant capable of producing seed having an embryo capable of producing in the presence 5-methyltryptophan at a concentration of $10^{-4}$ M roots of at least about 60 percent of the length of roots produced in the absence of 5-methyltryptophan, as measured after six days incubation, wherein the seed is capable of germinating into a plant capable of producing seed having an embryo capable of producing in the presence of 5-methyltryptophan at a concentration of $10^{-4}$ M roots of at least about 60 percent of the length of roots produced in the absence of 5-methyltryptophan, as measured after six days incubation.

26. A maize tissue culture derived from seeds deposited with In Vitro International, Inc. and assigned IVI accession No. 10010.

27. A maize tissue culture having an average endogenous free tryptophan content of at least about 0.78 milligrams per gram dry weight.

28. A method for producing a tryptophan overproducing maize plant, comprising the steps of:
   (a) isolating an appropriate donor tissue from a maize plant and growing said tissue in an initiation/maintenance medium to initiate and maintain the growth of plant tissue cultures;
   (b) growing said plant tissue cultures in the presence of a tryptophan analog at a level which inhibits from about 60% to about 80% of growth during the first four weeks;
   (c) repeated subculturing the plant tissue cultures of step (b) in the presence of the tryptophan analog;
   (d) identifying a stable analog resistant plant cell line from step (c) which grows at a rate comparable to that of a plant tissue culture grown in the absence of a tryptophan analog; and
   (e) regenerating a maize plant from said stable analog resistant plant cell line.

29. A method for producing hybrid maize seed, comprising crossing a first maize line capable of producing seed having an endogenous free tryptophan content of at least about one-tenth milligram per gram dry seed weight, and another maize line.

30. A method for producing hybrid maize seed, comprising crossing a first maize line capable of producing seed having an endogenous free tryptophan content of at least about one milligram per gram dry seed weight, and another maize line.

31. A method for producing hybrid maize seed, comprising crossing a first maize line capable of expressing a gene coding for an anthranilate synthase which retains from about 60 to about 80 percent of its activity in the presence of 5-methyltryptophan at a concentration of about $10^{-5}$ M, and another maize line.

32. A method for producing hybrid maize seed, comprising crossing a first maize line capable of producing seed having an embryo capable of producing in the presence of 5-methyltryptophan at a concentration of $10^{-4}$ M roots of at least about percent of the length of roots produced in the absence of 5-methyltryptophan, as measured after six days incubation, and another maize line.

* * * * *